US00PP30324P3

(12) United States Plant Patent
Gmitter, Jr.

(10) Patent No.: US PP30,324 P3
(45) Date of Patent: Apr. 2, 2019

(54) CITRUS TREE NAMED 'RBB7-34'

(50) Latin Name: ***Citrus reticulata* x *Citrus sinensis***
Varietal Denomination: RBB7-34

(71) Applicant: Florida Foundation Seed Producers, Inc., Marianna, FL (US)

(72) Inventor: Frederick G. Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 77 days.

(21) Appl. No.: 15/530,627

(22) Filed: Feb. 10, 2017

(65) Prior Publication Data

US 2018/0235124 P1 Aug. 16, 2018

(51) Int. Cl.
*A01H 5/08* (2018.01)
*A01H 6/78* (2018.01)

(52) U.S. Cl.
USPC ..... Plt./202
CPC ..... *A01H 6/785* (2018.05)

(58) Field of Classification Search
USPC ..... Plt./156, 201, 202
See application file for complete search history.

(56) References Cited

U.S. PATENT DOCUMENTS

PP21,356 P3 10/2010 Gmitter et al.
PP27,145 P3 9/2016 Grosser
PP27,829 P3 4/2017 Grosser

OTHER PUBLICATIONS

Citrus Budwood Annual Report 2015-2016. Florida Department of Agriculture and Consumer Services. https://www.freshfromflorida.com/content/download/72969/1974302/2015-2016_Annual_Report_Final.pdf. 5 pgs.*

Accession PI 539626, Germplasm Resources Information Network, Available at https://npgsweb.ars-grin.gov/gringlobal/accessiondetail.aspx?1434562, Retrieved Feb. 28, 2017.

* cited by examiner

*Primary Examiner* — Susan McCormick Ewoldt
*Assistant Examiner* — Karen M Redden
(74) *Attorney, Agent, or Firm* — Dentons US LLP

(57) ABSTRACT

The present invention relates to a new and distinct cultivar of *citrus* tree named 'RBB7-34'. This triploid cultivar arose from a cross of the seed parent 'LB8-9' with pollen from a tetraploid selection of 'Hamlin' sweet orange that arose from colchicine treated embryogenic callus. 'RBB7-34' produces fruit that resemble Navel orange in size, shape and with the presence of a navel on the blossom end of the fruit, but with greatly enhanced internal and external pigmentation compared with ordinary Navel orange cultivars grown in the humid, sub-tropical Florida climate. Fruit of RBB7-34 are seedless even under intensive cross pollination pressure.

7 Drawing Sheets

Latin name of the genus and species of the plant claimed: *Citrus reticulata* x *Citrus sinensis*.

Cultivar denomination: 'RBB7-34'.

BACKGROUND OF THE INVENTION

The present invention relates to a new and distinct cultivar of *citrus* tree named 'RBB7-34'. This triploid cultivar arose from a cross of the seed parent 'LB8-9' (U.S. Plant Pat. No. 21,356), which is a hybrid of 'Clementine' (unpatented) x 'Minneola' tangelo (unpatented) with pollen from a tetraploid selection of 'Hamlin' sweet orange (unpatented) that arose from colchicine treated embryogenic callus. Embryo rescue and culture were performed to recover a seedling plant in vitro from the under-developed embryo that typically results from interploid hybridization in *citrus*. A small shoot from the resulting in vitro seedling was then grafted to an etiolated 'Carrizo' citrange (unpatented) rootstock seedling, acclimated, then grown out in the greenhouse for a few years and finally planted in the field near Lake Alfred, Fla. The tree was first selected and propagated by top-working to a few pre-existing rootstock seedling hybrids directly in the same field; these top-worked trees fruited and produced true to type fruit. That and all other subsequent asexual propagations of 'RBB7-34' have remained true-to-type and retained the distinctive features of this novel triploid cultivar over successive generations.

SUMMARY OF THE INVENTION

The following are the most outstanding and distinguishing characteristics of 'RBB7-34'. The cultivar is triploid, in contrast to the diploid condition of 'Glen' Navel orange (unpatented). It produces fruit that resemble 'Glen' Navel orange in size, shape and with the presence of a navel on the blossom end of the fruit (~70% of the fruit), but with greatly enhanced internal and external pigmentation, compared with 'Glen' Navel orange cultivars grown in the humid, sub-tropical Florida climate (see FIGS. 4-7). 'RBB7-34' fruit more closely resemble fruit of 'Glen' Navel orange grown in a Mediterranean climate. In addition to improved color, 'RBB7-34' fruit also have substantially higher ° Brix and titratable acidity, compared to 'Glen' Navel orange cultivars grown in the same block and harvested at the same time (° Brix/acid=15.2-16.6/1.0 vs. 10.2/0.6, in December 2013). 'RBB7-34' fruit mature in the same season as the 'Glen' Navel orange, probably the most widely planted Navel cultivar in Florida, usually in December through January.

Though 'Glen' Navels are usually seedless, they can possess some seeds under high mixed cross pollination conditions. The fruit of 'RBB7-34' are seedless even under intensive cross pollination pressure. The fruit produced by 'RBB7-34' may be marketed as fresh fruit.

'RBB7-34' can be distinguished from its seed parent, 'LB8-9', and pollen parent, 'Hamlin', based at least upon their thorns and fruit. 'RBB7-34' exhibits larger and more conspicuous thorns than those of 'LB8-9' and 'Hamlin'. Also, unlike the fruit of 'LB8-9' and 'Hamlin', the fruit of 'RBB7-34' are seedless. Additionally, the fruit of 'RBB7-34' can be further distinguished by the absence of the characteristic conspicuous neck at stem ends of 'LB8-9' fruit.

BRIEF DESCRIPTION OF THE DRAWINGS

'RBB7-34' is illustrated by the accompanying photographs which show some aspects of the tree's form, foliage, and fruit. The colors shown are as true as can be reasonably obtained by conventional photographic procedures.

DETAILED BOTANICAL DESCRIPTION

Figure 1:
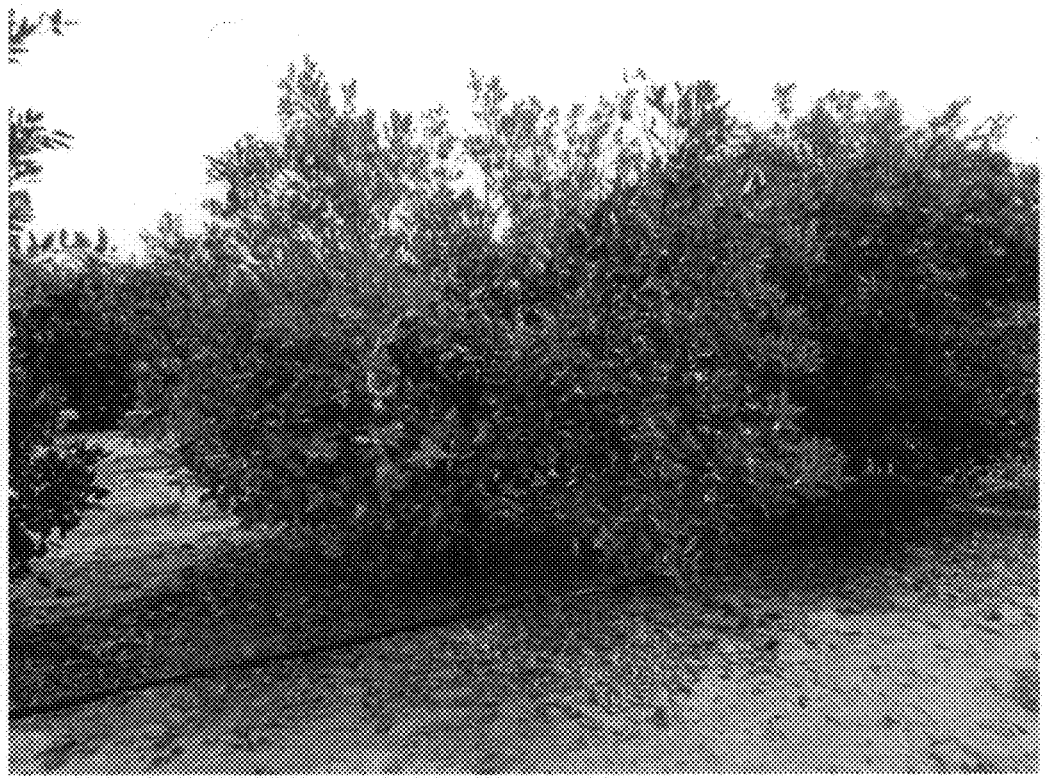
FIG. 1—Shows the overall mature plant growth and fruiting habit in December 2013. The tree was beginning to show the effects of *citrus* greening disease, or HLB, which was spreading rapidly through the orchard at this time.
Figure 2:
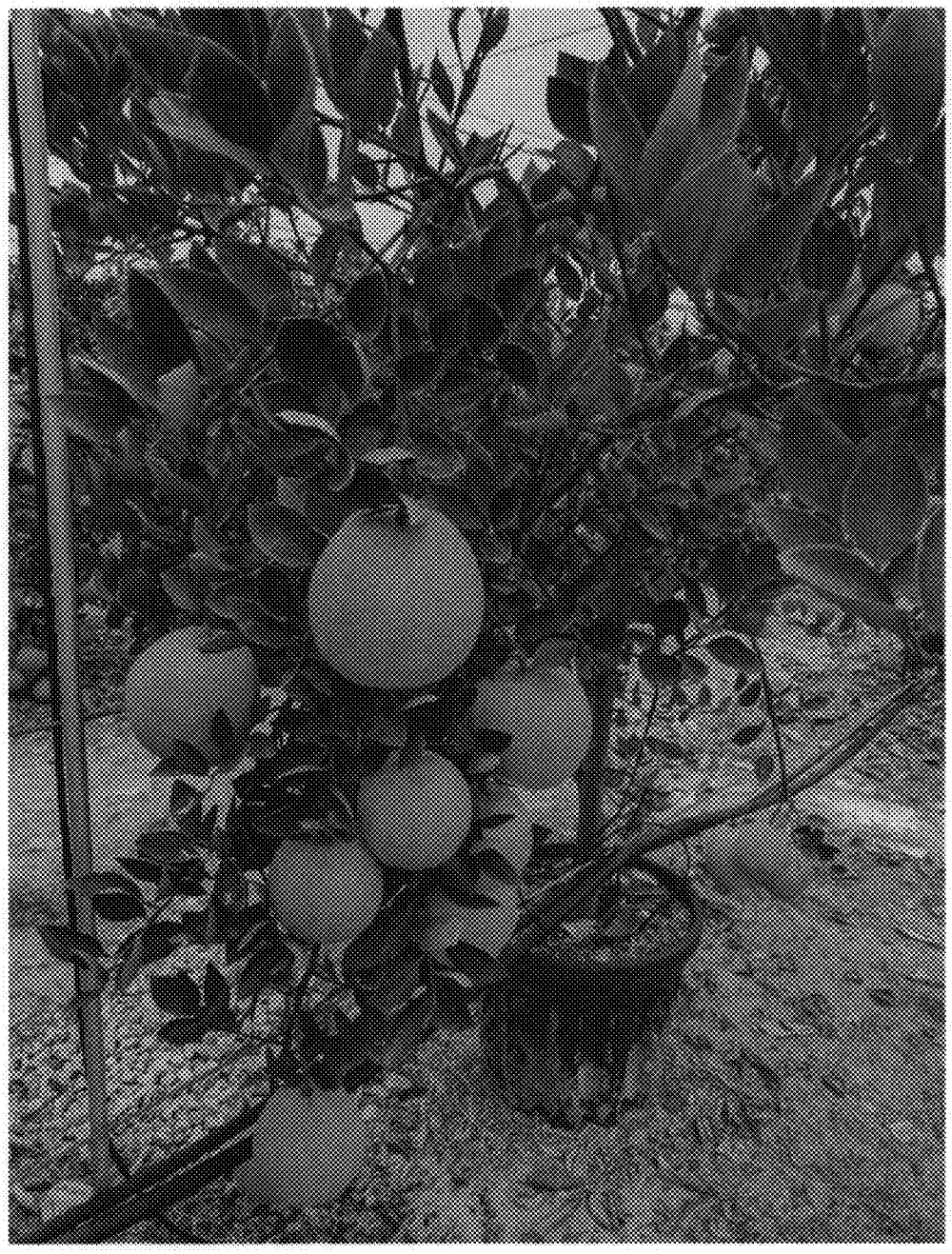
FIG. 2—Shows a young tree (~2 years) grown in a pot under open hydroponics management and in an enclosed structure. The photo was taken January 2017. The budwood source was very juvenile, as can be seen by the presence of conspicuous thorns. More mature budlines that have been developed are less thorny. The foliar characteristics are typical of those observed in triploid *citrus*, with thicker leaves and rougher texture resulting from larger oil glands, as opposed to the those commonly found on typical diploid navel orange trees.
Figure 3:
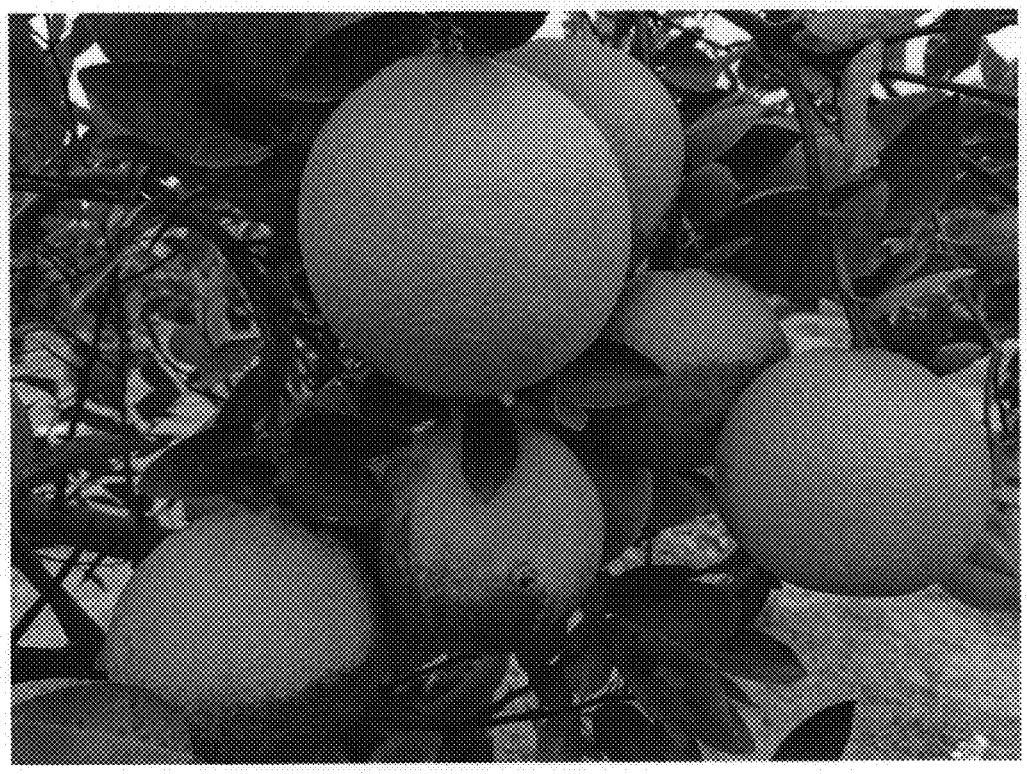
FIG. 3—Shows a cluster of mature fruit and leaves on another young tree (~2 years) tree grown in a pot under open hydroponics management and in an enclosed structure. The photo was taken January 2017. The budwood source was very juvenile, as can be seen by the presence of conspicuous thorns, as well as the more coarse texture of the fruit rind, typical characteristics of vigorous juvenile orange trees. The foliar characteristics are typical of those observed in triploid *citrus*, with thicker leaves and rougher texture resulting from larger oil glands, as opposed to the those commonly found on typical diploid navel orange trees.
Figure 4:
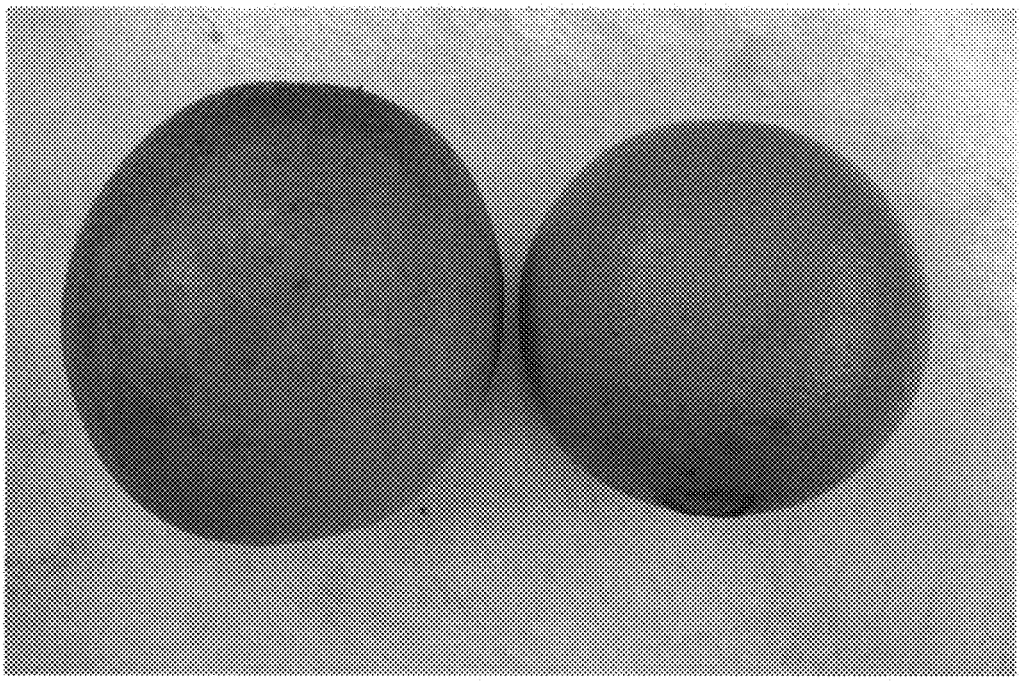
FIG. 4—Shows a close-up of the mature fruit, 'Glen' Navel left, characterized by pale green-yellow-orange color, and RBB7-34 right, characterized by deeper orange color. Photo taken December 2013.
Figure 5:
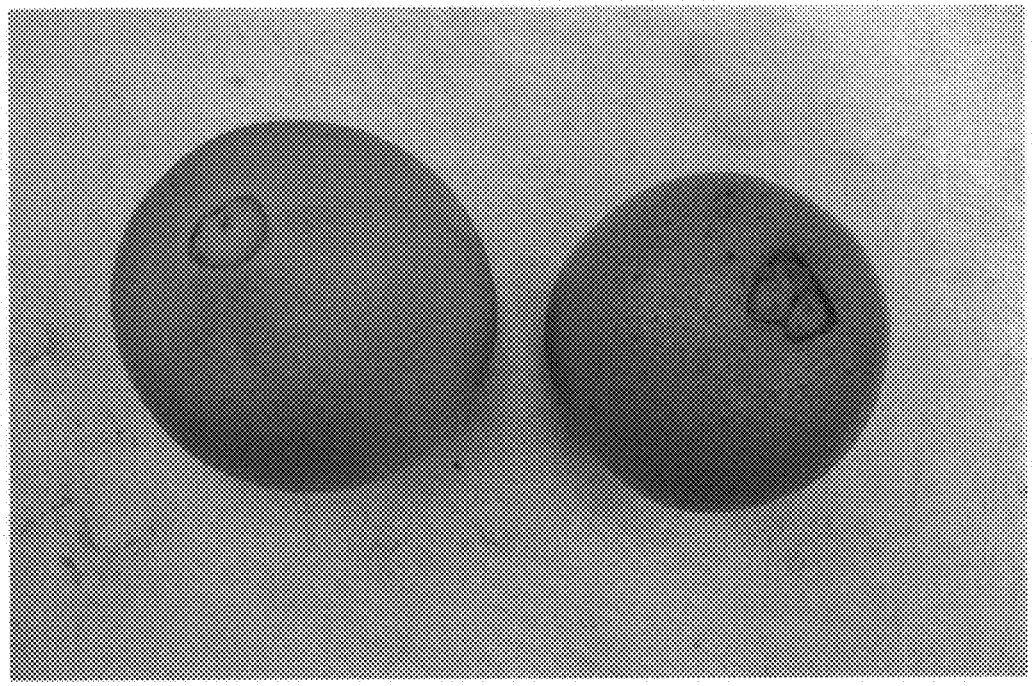
FIG. 5—Shows a close-up of the blossom, or navel, end of the mature fruit, 'Glen' Navel left, characterized by pale green-yellow-orange color, and RBB7-34 right, characterized by deeper orange color. Note the conspicuous navel structure of each. Photo taken December 2013.
Figure 6:
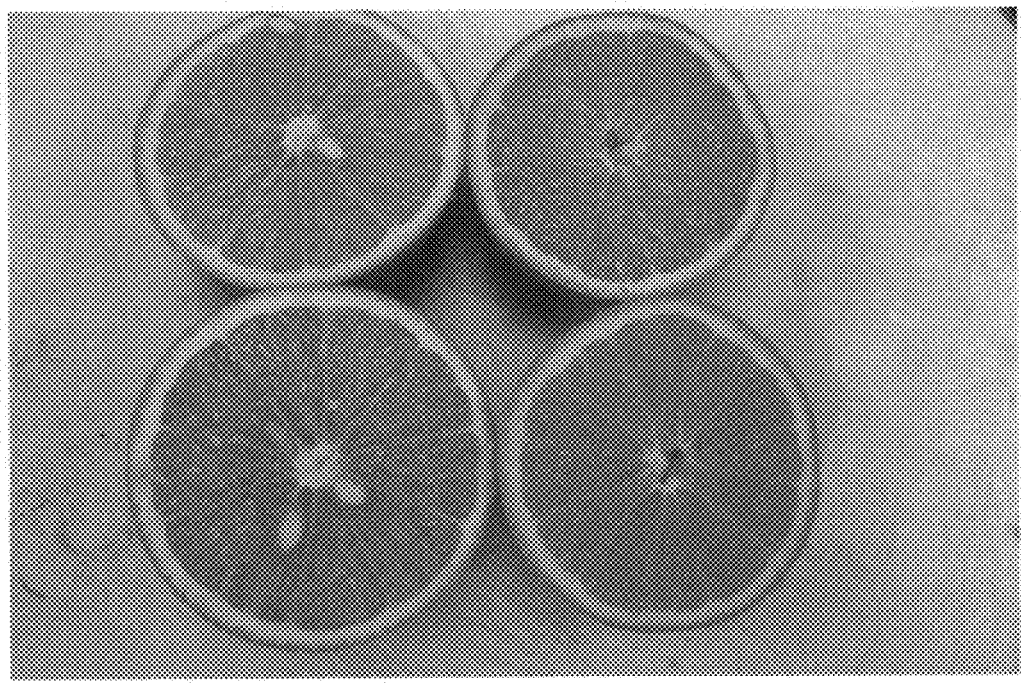
FIG. 6—Shows a close-up of the mature fruit cut equatorially, 'Glen' Navel left, characterized by pale yellow-orange flesh color and a few seeds, and RBB7-34 right, characterized by deeper orange color and the absence of seeds. Photo taken December 2013.
Figure 7:
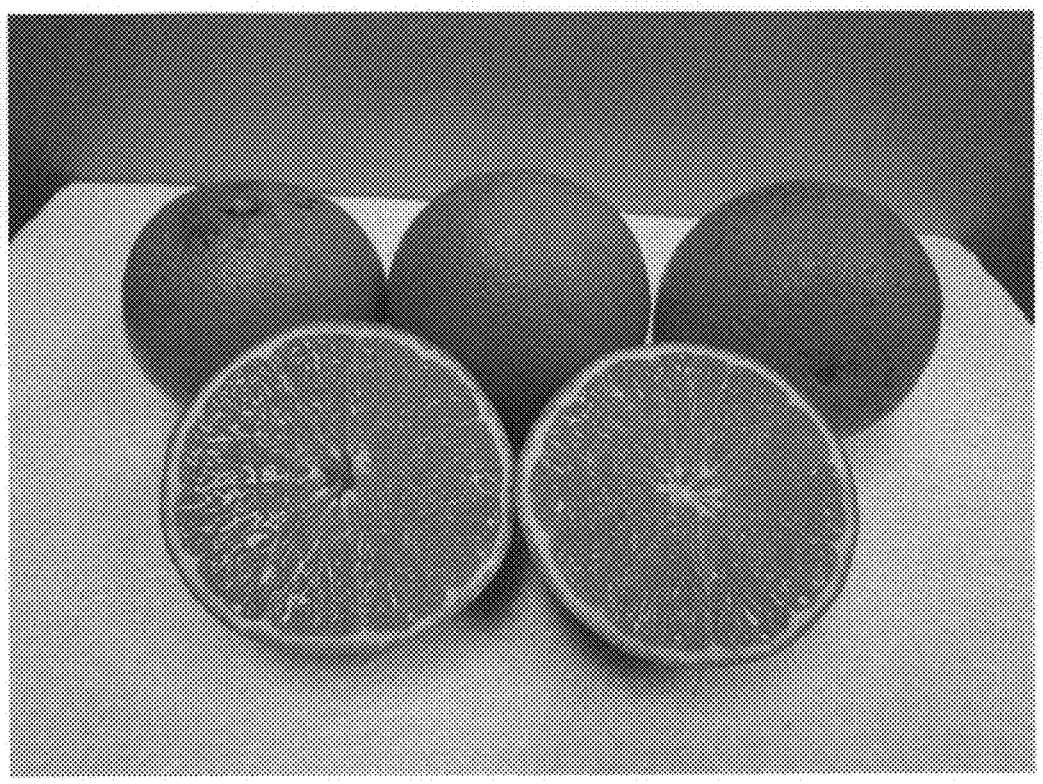
FIG. 7—Shows an additional close up of the mature fruit cut equatorially upfront, and 3 other fruit showing external color and appearance. Photo taken January 2014.

The following detailed description sets forth the distinctive characteristics of 'RBB7-34'. The present botanical description is that of the cultivar grown as a 7 year-old tree growing on 'Carrizo' rootstock in Lake Alfred, Fla. The colors (except those in common terms) are described from R.H.S. Colour Chart published by The Royal Horticultural Society in London (second edition), in association with the Flower Council of Holland.

PHENOTYPIC DESCRIPTION OF 'RBB7-34'

Classification:

*Botanical.*—*Citrus reticulata* x *Citrus sinensis.*

*Common name.*—Mandarange.

Parentage:

*Female parent.*—'LB8-9' (U.S. Plant Pat. No. 21,356) mandarin hybrid.

*Male parent.*—'Hamlin' sweet orange 4x, unreleased, unpatented breeding parent from the UF-CREC *citrus* breeding program.

Tree:

*Ploidy.*—Triploid.

*Size.*—Medium.

*Height.*—3.1 m.

*Tree spread.*—3.2 to 3.8 m.

*Vigor.*—Moderate vigorous.

*Density.*—Canopies are moderately dense.

*Form.*—Round-shaped with mostly lateral branches growing at low to medium angles. Branches with fruit exhibited drooping.

*Growth habit.*—Upright and lateral growth with low-medium angle.

Trunk:

*Trunk diameter.*—15 cm in diameter at 30 cm above from ground.

*Trunk texture.*—Rough with thorns.

*Trunk bark color.*—RHS N199A (greyed-brown); irregularly striated with RHS N189A (greyed-green).

Branches:

*Crotch angle.*—First crotch from 35- to 40-degree angle, middle crotch formed 120-degree angle.

*Branch length.*—3 m from the first crotch to the tip of the branch.

*Branch texture.*—Relatively rough with small thorns or spines.

*Branch color* (*shoots from previous flush, hardened, and* 4 *to* 5 *mm in diameter*).—RHS 138A (green).

Leaves:

*Size* (*lamina average*).—Length: 88.8 mm. Width: 53.2 mm. L/W ratio: 1.67.

*Thickness.*—Slightly thicker than regular and average mandarin leaves when compared to commercial mandarin hybrids, typical of triploid *citrus* hybrid plants.

*Arrangement.*—Alternately.

*Type.*—Simple.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS 137A (green). Lower surface (abaxial): RHS 146B (yellow-green).

*Petiole.*—Shape: Brevipetiolate (shorter than leaf lamina); junction between petiole and lamina is articulate. Width (petiole wing): Very narrow. Shape (petiole wing): Obovate. Length: 15 to 17 mm. Width: 3.6 to 3.9 mm. Color: RHS 137A (green).

Flowers and flower buds:

*Type*.—Hermaphrodite.

*Bearing*.—Flowers grown from leaf axillaries and leaf terminals in single flower and in small clusters of 1-3 flowers; most single flowers grown from leaf axillaries; each flower branch consists of 6 to 14 flowers.

*Flower diameter*.—Fully open flower with average diameter of 38.2 to 38.6 mm.

*Flower depth*.—Typical flower with average depth of 16.2 mm.

*Flower blooming period*.—First bloom observed: Feb. 20, 2012. Full bloom observed: Feb. 25, 2012.

*Flower bud size*.—Length: Initial visible flower bud with 2.8 mm in length; mature flower bud with 20 mm in length. Diameter: Initial visible flower bud with 3.0 mm in diameter; mature flower bud with 20 mm in diameter.

*Flower bud shape*.—Initial visible flower bud: Round ball shape. Mature flower bud: Elongated olive shape.

*Flower bud color*.—Initial visible flower bud: RHS 138B (green). Mature flower bud: RHS NN155C (white) with RHS 151C (yellow-green) spots distributed at tip of the flower bud.

*Flower petals*.—Shape: Flat spatula shaped Apex shape: Smooth acute shaped. Base shape: Even obtuse. Color: Upper surface with RHS NN155C (white); lower surface with RHS NN155B (white) with RHS 151C yellow-green) spots distributed toward to the petal apex. Margin: Smooth.

*Flower sepal*.—Number: 5 per flower. Shape: Delta shaped with acute angle at apex. Length: 3.8 mm. Width: 3.6 mm. Apex shape: Triangle-shaped. Margin: Smooth. Color: Upper surface with RHS 145D (yellow-green); lower surface with RHS 145C (yellow-green).

*Fragrance*.—Moderately fragrant.

*Flower pedicel*.—Length: 7.2 to 7.8 mm. Diameter: 1.5 to 1.7 mm. Color: RHS 145B (yellow-green).

*Reproductive organs*.—Fertility: Appears self-fertile. Stamen length: 13.6 to 13.8 mm. Anther length: 3.6 mm. Anther Width: 1.2 to 1.4 mm. Anther color: RHS 22D (yellow-orange). Anther filament length: 10 to 11.2 mm. Pollen amount: Low. Pollen color (general): RHS 16A (yellow-orange). Pistil number: 1. Pistil length: 13.2 to 13.5 mm. Pistil color: RHS 145D (yellow-green). Style length: 9 mm. Style diameter: 1.8 to 1.9 mm. Style color: RHS 145D (yellow-green). Ovary shape: Oval-shaped. Ovary diameter: 3.9 mm. Ovary color: RHS 143C (green).

Fruit:

*Size*.—Uniform.

*Average height*.—73.1 to 75 mm.

*Average width*.—79.1 to 81.5 mm.

*Average weight* (*per individual fruit*).—238.5 g.

*Shape*.—Round.

*Shape* (*cross-section*).—Round.

*Apex*.—Truncated, 70% of the fruit appear to have navel.

*Base cavity diameter*.—6.8 to 7.0 mm.

*Base*.—No neck.

*Harvesting*.—First pick around December 20th based on season and rootstock; last pick around late January though fruit continue to hold on the tree for a longer time (based on season and rootstock).

*Fruit stem* (*short stem connecting the fruit*).—Length: 7.9 to 9.9 mm. Diameter: 4.0 to 5.0 mm. Color: RHS 195A (greyed-green) with RHS 197A (greyed-green) strip.

Rind:

*Adherence*.—Albedo (mesocarp) to flesh (endocarp) is medium-strong, similar to regular navel sweet orange, and is evenly distributed from base to apex.

*Thickness*.—2.7 to 3.4 mm.

*Texture*.—Smooth.

*Color*.—Flavedo (epicarp): Ranges from RHS 23A (yellow-orange) to RHS 24B (orange). Albedo (mesocarp): RHS 18C (yellow-orange).

*Stylar end*.—Slightly open and 70% of the fruit have navel.

*Rind oil cell density*.—206 oil cells/square cm.

Flesh:

*Number of segments*.—Average between 11 to 12 segments per fruit.

*Segment walls*.—Medium-soft with sufficient strength to maintain integrity as separated.

*Juice*.—Abundant.

*Color*.—Uniformly RHS 23A (yellow-orange).

*Texture*.—Medium-soft.

*Vesicles*.—Length: 12.2 to 13.3 mm. Diameter (thickness): 3.5 to 4 mm.

*Eating quality* (*tested at mid-december*).—Soluble solids (average): 15.2 to 15.4 Brix. Acidity (average): 1.0 to 1.2. Ratio: 12.7.

Seeds:

*Type*.—Seedless.

Disease and insect resistance: Susceptible to Asian *citrus* canker and to Huanglongbing (HLB or *citrus* greening).

What is claimed is:

1. A new and distinct *citrus* tree called 'RBB7-34' as illustrated and described herein.

* * * * *